(12) United States Patent
Yamada et al.

(10) Patent No.: US 8,138,668 B2
(45) Date of Patent: Mar. 20, 2012

(54) BENZO[A]FLUORANTHENE COMPOUND AND ORGANIC LIGHT EMITTING DEVICE USING THE SAME

(75) Inventors: Naoki Yamada, Inagi (JP); Satoshi Igawa, Fujisawa (JP); Masashi Hashimoto, Tokyo (JP); Minako Nakasu, Tokyo (JP); Takayuki Horiuchi, Tokyo (JP); Jun Kamatani, Tokyo (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 237 days.

(21) Appl. No.: 12/438,894

(22) PCT Filed: May 15, 2008

(86) PCT No.: PCT/JP2008/059393
§ 371 (c)(1),
(2), (4) Date: Feb. 25, 2009

(87) PCT Pub. No.: WO2008/140134
PCT Pub. Date: Nov. 20, 2008

(65) Prior Publication Data
US 2010/0019661 A1    Jan. 28, 2010

(30) Foreign Application Priority Data

May 16, 2007 (JP) .................. 2007-130526
Apr. 2, 2008 (JP) .................. 2008-095673

(51) Int. Cl.
*H01J 1/63* (2006.01)
*C07C 25/13* (2006.01)
(52) U.S. Cl. ....................... 313/504; 570/129
(58) Field of Classification Search .................. 428/690, 428/917, 411.1, 336; 257/40, 88, 104, E51; 585/27; 313/502–509; 570/129; 546/4
See application file for complete search history.

(56) References Cited

U.S. PATENT DOCUMENTS
2003/0027016 A1  2/2003  Ara et al. ...................... 428/690
(Continued)

FOREIGN PATENT DOCUMENTS
JP         10-189247        7/1998
(Continued)

OTHER PUBLICATIONS
Huang, et al. Chem. Mater. 2003, 15, 4854-4862.*
(Continued)

*Primary Examiner* — Angela Ortiz
*Assistant Examiner* — J. L. Yang
(74) *Attorney, Agent, or Firm* — Fitzpatrick, Cella, Harper & Scinto

(57) ABSTRACT

There is provided a benzo[a]fluoranthene compound represented by the following general formula (I): wherein at least one of $R_{14}$, $R_{15}$, $R_{16}$, $R_{20}$, and $R_{21}$ represents $R_n$ represented by the following general formula (i), and $R_{11}$ to $R_{22}$ none of which is represented by $R_n$ each represent a hydrogen atom, a halogen atom or the like, and $R_{11}$ to $R_{22}$ none of which is represented by $R_n$ may be identical to or different from one another; wherein $R_{23}$, $R_{24}$, $R_{25}$, $R_{26}$, and $R_{27}$ each represent a hydrogen atom, a halogen atom or the like, and $R_{23}$, $R_{24}$, $R_{25}$, $R_{26}$, and $R_{27}$ may be identical to or different from one another, provided that, in at least one pair of adjacent substituents out of $R_{23}$, $R_{24}$, $R_{25}$, and $R_{26}$, the substituents are bonded to each other to form a ring.

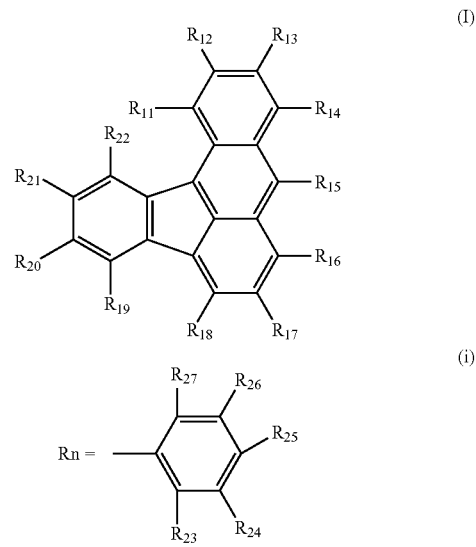

7 Claims, 3 Drawing Sheets

U.S. PATENT DOCUMENTS

| | | | |
|---|---|---|---|
| 2004/0076853 A1* | 4/2004 | Jarikov | 428/690 |
| 2005/0238920 A1* | 10/2005 | Sotoyama et al. | 428/690 |
| 2007/0249878 A1 | 10/2007 | Iwawaki et al. | 585/27 |
| 2007/0252141 A1 | 11/2007 | Negishi et al. | 257/40 |
| 2008/0272692 A1 | 11/2008 | Hashimoto et al. | 313/504 |
| 2008/0286611 A1 | 11/2008 | Muratsubaki et al. | 428/704 |
| 2009/0033210 A1 | 2/2009 | Saitoh et al. | 313/504 |
| 2009/0066227 A1 | 3/2009 | Okinaka et al. | 313/504 |
| 2009/0079344 A1 | 3/2009 | Saitoh et al. | 313/504 |
| 2009/0102371 A1 | 4/2009 | Hashimoto et al. | 313/504 |
| 2009/0134788 A1 | 5/2009 | Yamada et al. | 313/504 |
| 2010/0237328 A1* | 9/2010 | Horiuchi et al. | 257/40 |
| 2011/0049479 A1* | 3/2011 | Yamada et al. | 257/40 |

FOREIGN PATENT DOCUMENTS

| | | |
|---|---|---|
| JP | 10-340785 | 12/1998 |
| JP | 2002-008867 | 1/2002 |
| JP | 2002069044 | 3/2002 |
| JP | 2003/347058 | 12/2003 |
| JP | 2004002351 | 1/2004 |
| JP | 2007027356 | 2/2007 |

OTHER PUBLICATIONS

U.S. Appl. No. 12/438,629, filed May 15, 2008.
U.S. Appl. No. 12/438,640, filed May 15, 2008.
U.S. Appl. No. 12/295,240, filed Mar. 13, 2007.
U.S. Appl. No. 12/296,574, filed Oct. 9, 2008.
Steven L. Murov, et al., "Handbook of Photochemistry (Second Edition, Revised and Expanded)," Photophysics of Organic Molecules in Solution, pp. 1-3, 8-11, 14-15, 20-21, 26-27, and 36-37, (1993).
N.I. Nijegorodov et al., "The Journal of Physical Chemistry," The Influence of Planarity and Rigidity on the Absorption and Fluorescence Parameters and Intersystem Crossing Rate Constant in Aromatic Molecules, vol. 98, No. 22, 1994, pp. 5639-5643.
Tai-Hsiang Huang, et al., "Chemistry of Material," Benzo[a]aceanthrylene Derivatives for Red-Emitting Electroluminescent Materials, 2003, vol. 15, No. 25, p. 4854-4862.
International Preliminary Report on Patentability for PCT/JP2008/059393, issued Nov. 26, 2009, 5 pages.

* cited by examiner

BENZO[A]FLUORANTHENE COMPOUND AND ORGANIC LIGHT EMITTING DEVICE USING THE SAME

TECHNICAL FIELD

The present invention relates to a benzo[a]fluoranthene compound and an organic light emitting device using the compound.

BACKGROUND ART

An organic light emitting device is a device in which a thin film including a fluorescent organic compound or a phosphorescent organic compound is sandwiched between an anode and a cathode. Further, electrons and holes are injected from the respective electrodes to generate exciton of the fluorescent compound or the phosphorescent compound, whereby the organic light emitting device emits light when the exciton return to a ground.

Recent progress of an organic light emitting device is remarkable, and the characteristics of the device enable a light emitting device with a high luminance at a low applied voltage, a variety of emission wavelengths, high-speed responsiveness, thin and light weight. From this fact, it is suggested that the device have potential to find use in a wide variety of applications.

However, the present situation calls for optical output with even higher luminance or higher conversion efficiency. In addition, many problems still remain to be solved regarding durability against the change over time due to long-term use, deterioration caused by atmospheric gas containing oxygen, moisture, or the like.

Further, when considering application to a full color display or similar device, the present art is still insufficient against problems relating to the needs for light emission of blue, green, and red with a high color purity.

The use of a benzofluoranthene compound as a component for an organic light emitting device has been proposed as a method of solving the above-mentioned problems. For example, in each of Japanese Patent Application Laid-Open No. H10-189247, Japanese Patent Application Laid-Open No. 2002-8867, and Chem. Master. 2003, 15, 4854-4862, a benzofluoranthene compound is used as a component for an organic light emitting device.

DISCLOSURE OF THE INVENTION

An object of the present invention is to provide a novel benzo[a]fluoranthene compound. Another object of the present invention is to provide an organic light emitting device having extremely good light emitting efficiency, extremely good luminance, and durability.

A benzo[a]fluoranthene compound of the present invention is represented by the following general formula (I).

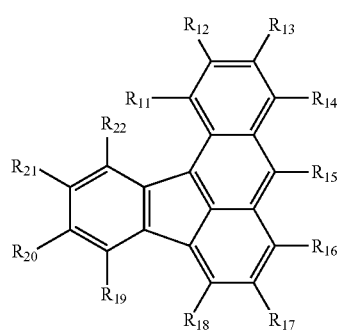

(I)

wherein:

at least one of $R_{14}$, $R_{15}$, $R_{16}$, $R_{20}$ and $R_{21}$ represents $R_n$, represented by the following general formula (i):

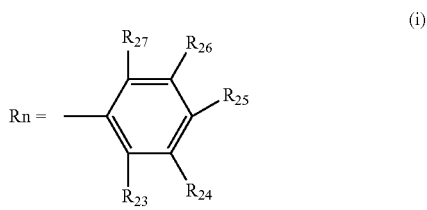

(i)

wherein $R_{23}$, $R_{24}$, $R_{25}$, $R_{26}$, and $R_{27}$ each represent a hydrogen atom, a halogen atom, a cyano group, a nitro group, a substituted or unsubstituted alkyl group, a substituted or unsubstituted alkoxy group, a substituted or unsubstituted aryloxy group, a substituted or unsubstituted alkenyl group, a substituted or unsubstituted alkynyl group, a substituted or unsubstituted aralkyl group, a substituted or unsubstituted amino group, a substituted or unsubstituted aryl group, or a substituted or unsubstituted heterocyclic group, and $R_{23}$, $R_{24}$, $R_{25}$, $R_{26}$, and $R_{27}$ may be identical to or different from one another, provided that, in at least one pair of adjacent substituents out of $R_{23}$, $R_{24}$, $R_{25}$, and $R_{26}$, the substituents are bonded to each other to form a ring.

According to the present invention, there can be provided a novel benzo[a]fluoranthene compound. In addition, according to the present invention, there can be provided an organic light emitting device having extremely good light emitting efficiency, extremely good luminance, and durability.

Further features of the present invention will become apparent from the following description of exemplary embodiments with reference to the attached drawings.

BEST MODE FOR CARRYING OUT THE INVENTION

Figure 1:
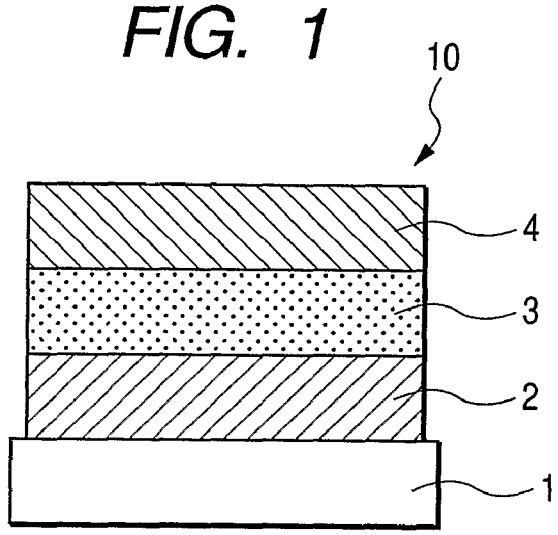
FIG. 1 is a cross sectional view illustrating an organic light emitting device according to a first embodiment of the present invention.

First, a benzo[a]fluoranthene compound of the present invention will be described.

First, a first embodiment of the benzo[a]fluoranthene compound of the present invention will be described. Here, the first embodiment of the benzo[a]fluoranthene compound of the present invention is a compound represented by the following general formula (I).

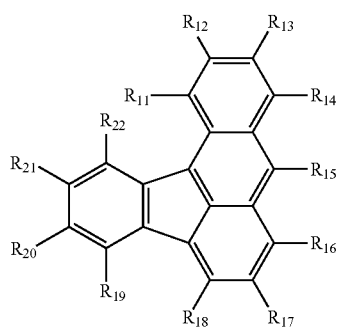

(I)

In the general formula (I), at least one of $R_{14}$, $R_{15}$, $R_{16}$, $R_{20}$, and $R_{21}$ represents $R_n$, represented by the following general formula (i); $R_{15}$ preferably represents $R_n$.

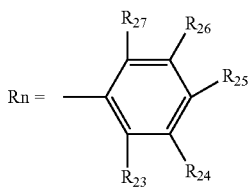

(i)

wherein $R_{23}$, $R_{24}$, $R_{25}$, $R_{26}$, and $R_{27}$ each represent a hydrogen atom, a halogen atom, a cyano group, a nitro group, a substituted or unsubstituted alkyl group, a substituted or unsubstituted alkoxy group, a substituted or unsubstituted aryloxy group, a substituted or unsubstituted alkenyl group, a substituted or unsubstituted alkynyl group, a substituted or unsubstituted aralkyl group, a substituted or unsubstituted amino group, a substituted or unsubstituted aryl group, or a substituted or unsubstituted heterocyclic group, and $R_{23}$, $R_{24}$, $R_{25}$, $R_{26}$, and $R_{27}$ may be identical to or different from one another, provided that, in at least one pair of adjacent substituents out of $R_{23}$, $R_{24}$, $R_{25}$, and $R_{26}$, the substituents are bonded to each other to form a ring. The number of combination of adjacent substituents to from a ring may be two or more.

$R_n$ represented by any one of $R_{14}$, $R_{15}$, $R_{16}$, $R_{20}$, and $R_{21}$ refers to, for example, a fused polycyclic group. Specific examples of the fused polycyclic group include a naphthyl group, an azulenyl group, a pentalenyl group, an indenyl group, a pyrenyl group, an indacenyl group, an acenaphthenyl group, a phenanthryl group, a phenalenyl group, a fluoranthenyl group, a benzofluoranthenyl group, an acephenanthryl group, an aceanthryl group, a triphenylenyl group, a chrysenyl group, a perylenyl group, a fluorenyl group, an imidazolyl group, a carbazolyl group, an acridinyl group, and a phenanthrolyl group. Of those, a fluorenyl group, a fluoranthenyl group, a benzofluoranthenyl group, a pyrenyl group, or a perylenyl group is preferable.

Examples of the substituent which $R_n$ described above may have include: alkyl groups such as a methyl group, an ethyl group, a propyl group, and a t-butyl group; alkenyl groups such as a vinyl group, a propenyl group, a butenyl group, a phenylvinyl group, and a diphenylvinyl group; alkynyl groups such as an ethynyl group, a propynyl group, a butynyl group, and a phenethynyl group; aralkyl groups such as a benzyl group and a phenethyl group; aryl groups such as a phenyl group, a biphenyl group, a fluorenyl group, a fluoranthenyl group, a benzofluoranthenyl group, a 3,5-di-t-butylphenyl group, a 2,4,6-trimethylphenyl group, a 4-t-butylphenyl group, a 3,5-dimethylphenyl group, a 9,9-dimethyl-9H-fluorenyl group, and a tolyl group; heterocyclic groups such as a thienyl group, a pyrrolyl group, and a pyridyl group; amino groups such as a dimethylamino group, a diethylamino group, a dibenzylamino group, a diphenylamino group, a ditolylamino group, a dianisolylamino group, a phenylnaphthylamino group, and a di-(4-t-butylphenyl)amino group; alkoxy groups such as a methoxy group, an ethoxy group, a propoxy group, and a phenoxy group; aryloxycyano groups such as a phenoxy group, a 4-methylphenoxy group, and a naphthoxy group; a nitro group; and halogen atoms such as fluorine and chlorine.

$R_{14}$, $R_{15}$, $R_{16}$, $R_{20}$, and $R_{21}$ none of which is represented by $R_n$, $R_{23}$ to $R_{27}$ none of which contributes to the formation of a ring, and $R_{11}$ to $R_{13}$, $R_{17}$ to $R_{19}$, and $R_{22}$ described above each represent a hydrogen atom, a halogen atom, a cyano group, a nitro group, a substituted or unsubstituted alkyl group, a substituted or unsubstituted alkoxy group, a substituted or unsubstituted aryloxy group, a substituted or unsubstituted alkenyl group, a substituted or unsubstituted alkynyl group, a substituted or unsubstituted aralkyl group, a substituted or unsubstituted amino group, a substituted or unsubstituted aryl group, or a substituted or unsubstituted heterocyclic group.

Examples of the halogen atom include fluorine, chlorine, bromine, and iodine.

Examples of the alkyl group include a methyl group, an ethyl group, a normal-propyl group, an isopropyl group, a normal butyl group, a tertiary butyl group, a secondary butyl group, an octyl group, a 1-adamanthyl group, and a 2-adamanthyl group.

Examples of the alkoxy group include a methoxy group, an ethoxy group, and a propoxy group.

Examples of the aryloxy group include a phenoxy group, a 4-methylphenoxy group, and a naphthoxy group.

Examples of the alkenyl group include a vinyl group, a propenyl group, a butenyl group, a phenylvinyl group, and a diphenylvinyl group.

Examples of the alkynyl group include an ethinyl group, a propinyl group, a butinyl group, and a phenethynyl group.

Examples of the aralkyl group include a benzyl group and a phenethyl group.

Examples of the amino group include a dimethylamino group, a diethylamino group, a dibenzylamino group, a diphenylamino group, a ditolylamino group, a ditertial butylamino group, a dianisolylamino group, and a carbazoyl group.

Examples of the aryl group include a phenyl group, a biphenyl group, a terphenyl group, a naphthyl group, an azulenyl group, a pentalenyl group, an indenyl group, a pyrenyl group, an indacenyl group, an acenaphthenyl group, a phenalenyl group, a fluoranthenyl group, a benzofluoranthenyl group, an acephenanthryl group, an aceanthryl group, a triphenylenyl group, a chrysenyl group, a perylenyl group, and a fluorenyl group.

Examples of the heterocyclic group include a thienyl group, a pyrrolyl group, a pyridyl group, a pyrimidyl group, a bipyridyl group, an oxazolyl group, an oxadiazolyl group, a thiazolyl group, a thiadiazolyl group, a terthienyl group, an imidazolyl group, a carbazolyl group, an acridinyl group, and a phenanthrolyl group.

Specific examples of the substituent which each of the halogen atom, the alkyl group, the alkoxy group, the aryloxy group, the alkenyl group, the alkynyl group, the aralkyl group, the amino group and the alkyl group may have described above are identical to examples of the substituent which $R_n$ in the general formula (I) may have. In addition, $R_{14}$, $R_{15}$, $R_{16}$, $R_{20}$, and $R_{21}$ none of which is represented by $R_n$, $R_{23}$ to $R_{27}$ none of which contributes to the formation of a ring, and $R_{11}$ to $R_{13}$, $R_{17}$ to $R_{19}$, and $R_{22}$ may be identical to or different from one another.

When the benzo[a]fluoranthene compound of the present invention is used as a light emitting material for an organic light emitting device, the emission quantum efficiency of benzo[a]fluoranthene as a material mainly responsible for light emission is desirably large in order that the light emitting efficiency of the organic light emitting device may be improved.

However, a molecule itself of unsubstituted benzo[a]fluoranthene has low fluorescent quantum efficiency, so a substituent that improves the fluorescent quantum efficiency of the molecule itself must be introduced into the benzofluoranthene skeleton of the molecule. Here, Table 1 below shows the fluorescent quantum efficiency of each of various compounds themselves each containing benzo[a]fluoranthene. It should be noted that, in Table 1 below, the fluorescent quantum efficiency of benzo[a]fluoranthene is an experimental value, and the fluorescent quantum efficiency of any compound except benzo[a]fluoranthene is a numerical value described in Steaven L. Murov, Ian Carmichael, Gordon L. Hug, Handbook of Photochemistry, 1993.

TABLE 1

| Compound | Fluorescent quantum efficiency |
| --- | --- |
| Benzo[a]fluoranthene | 0.19 |
| Fluorene | 0.68 |
| Fluoranthene | 0.35 |
| Benzo[k]fluoranthene | 1.0 |
| Perylene | 0.77 |
| Benzene | 0.06 |
| Biphenyl | 0.15 |
| Triphenylamine | 0.045 |

As can be seen from Table 1 above, fluorene, fluoranthene, benzo[k]fluoranthene, pyrene, and perylene each having such a structure that Rn in the general formula (I) is represented by the general formula (i) each have higher fluorescent quantum efficiency than that of benzo[a]fluoranthene. Accordingly, the introduction of at least one substituent originating from any one of those compounds into the benzo[a]fluoranthene skeleton improves the fluorescent quantum efficiency of the benzo[a]fluoranthene compound.

On the other hand, as can be seen from Table 1 above, benzene and triphenylamine which belongs to biphenylamines each have lower fluorescent quantum efficiency than that of benzo[a]fluoranthene. Accordingly, even the introduction of a substituent originating from any one of those compounds into the benzo[a]fluoranthene skeleton does not improve the fluorescent quantum efficiency of the benzo[a]fluoranthene compound.

In addition, when Rn in the general formula (I) represents anthracene using 9-position as a bonding hand, the introduction of such anthracene into the benzo[a]fluoranthene skeleton does not show any improvement in fluorescent quantum efficiency of the benzo[a]fluoranthene compound. In particular, the introduction of an anthracene skeleton using 9-position as a bonding hand into $R_{15}$ in the general formula (I) results in excessively large steric repulsion between the benzo[a]fluoranthene skeleton and the anthracene skeleton. Therefore, it is not desirable that $R_{27}$ which may be bonded to $R_{26}$ to form an anthracene skeleton using 9-position as a bonding hand in $R_n$, of the general formula (i) contribute to the formation of a ring.

In addition, a substituent that improves the fluorescent quantum efficiency of the benzo[a]fluoranthene compound is preferably introduced into any one of $R_{14}$, $R_{15}$, $R_{16}$, $R_{20}$, and $R_{21}$ in the general formula (I). Multiple substituents of the above kind may be introduced as long as each of the substituents is introduced into any one of $R_{14}$, $R_{15}$, $R_{16}$, $R_{20}$, and $R_{21}$. The introduction of the substituent into any one of those positions is identical to the introduction of the substituent in the direction of the transition moment of the benzo[a]fluoranthene compound itself. The introduction of the substituent additionally improves the fluorescent quantum efficiency of the benzo[a]fluoranthene compound because the introduction enlarges the transition moment of the benzo[a]fluoranthene compound.

Hereinafter, specific examples of the compound represented by the general formula (I) will be shown below. However, the present invention is not limited to these examples.

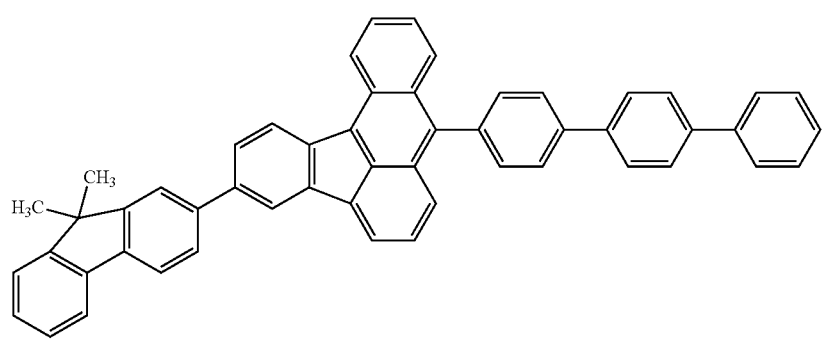

C-1

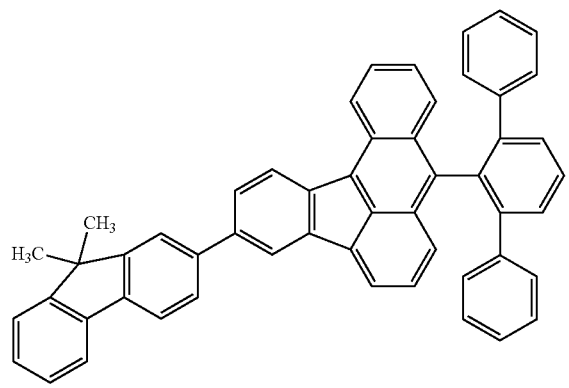
C-2
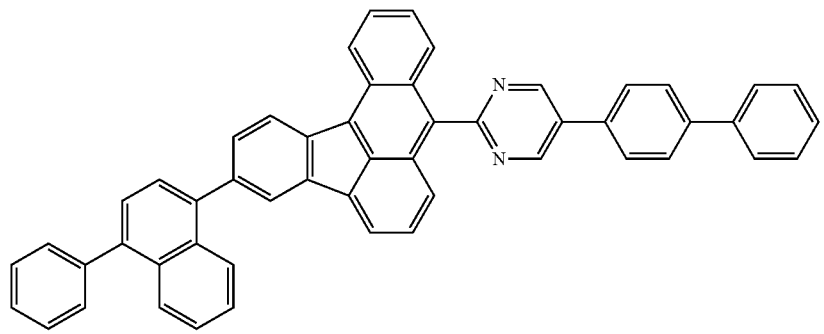
C-3
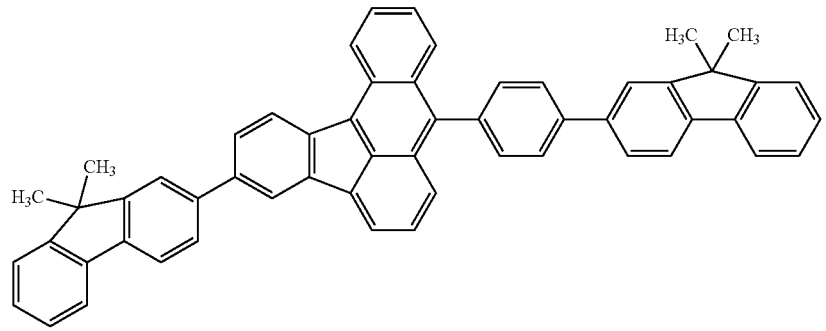
C-4
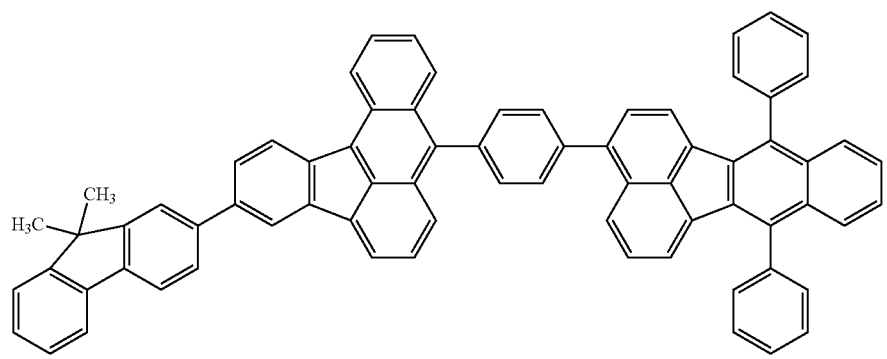
C-5

-continued
C-6
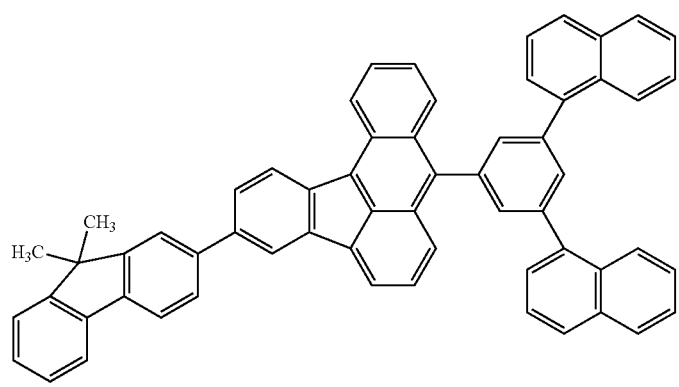
C-7
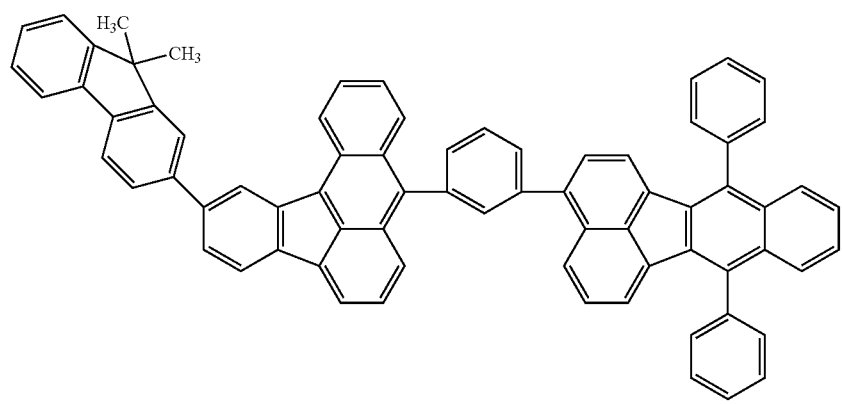
C-8
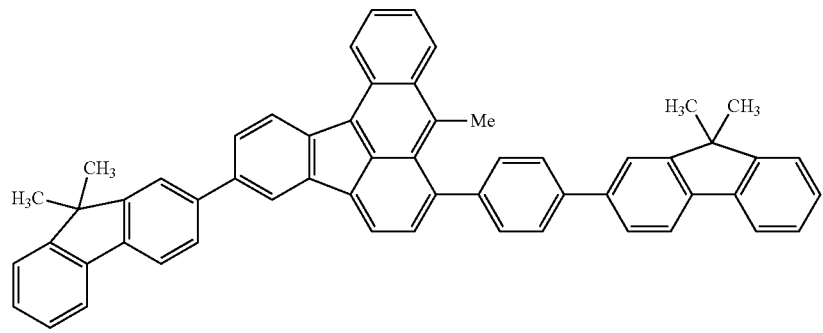
D-1
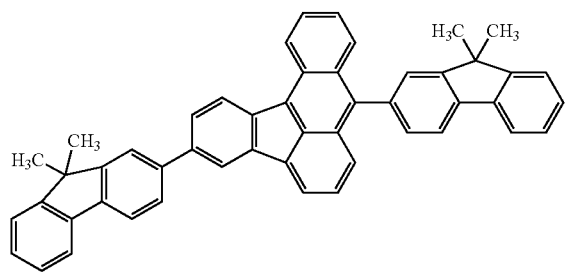
D-2
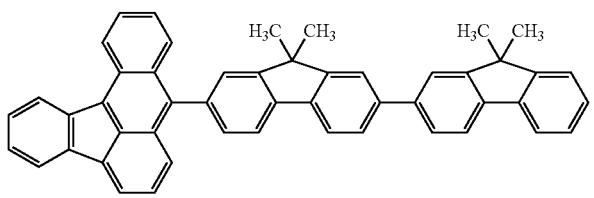

-continued
D-3
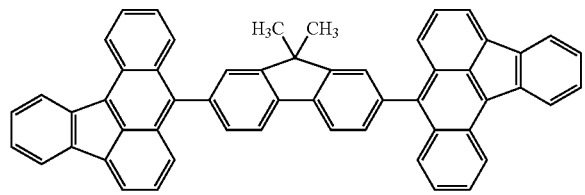
D-4
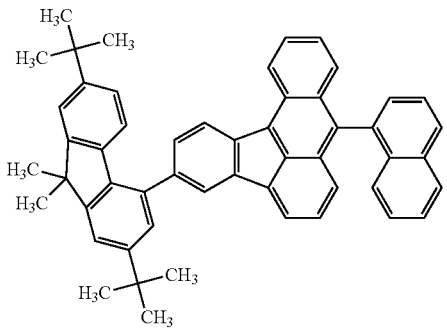
D-5
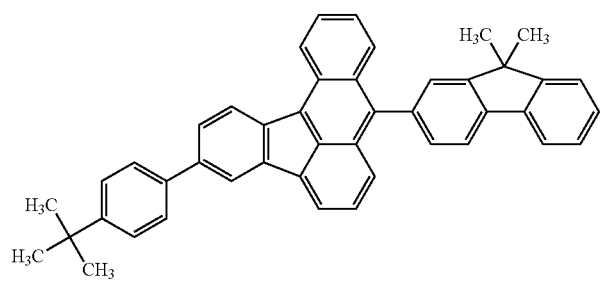
D-6
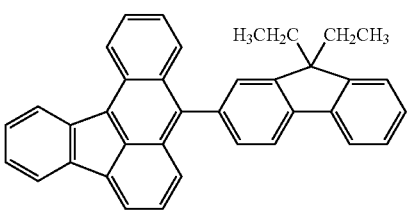
D-7
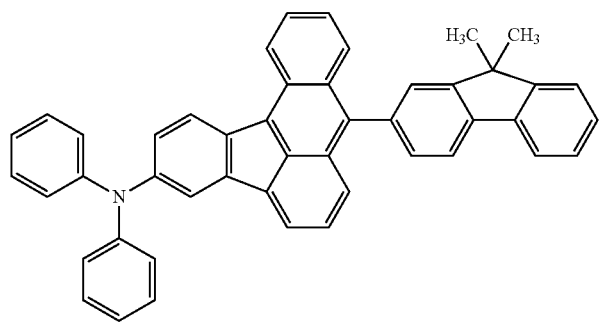
D-8
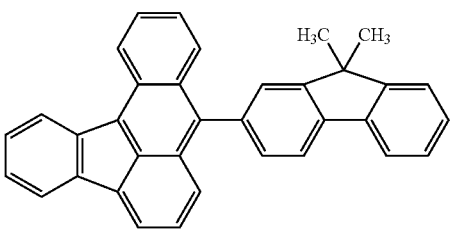
D-9
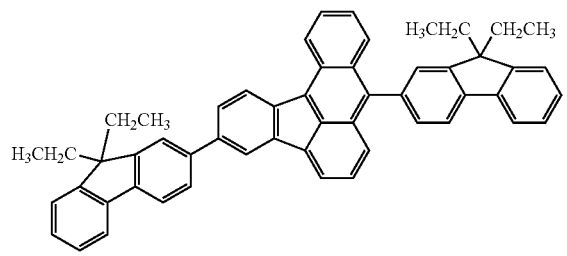
D-10
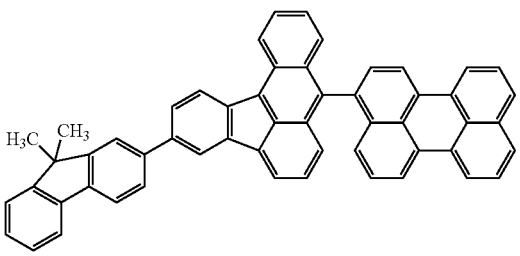
D-11
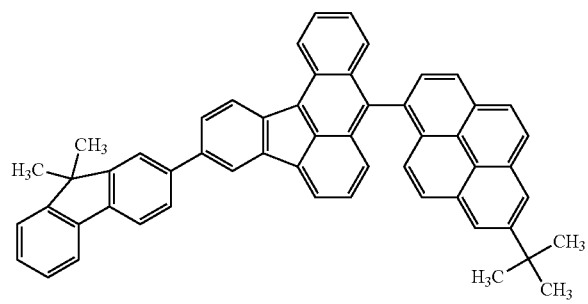
D-12
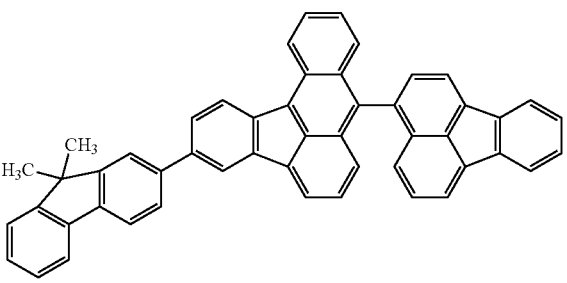

-continued
D-13
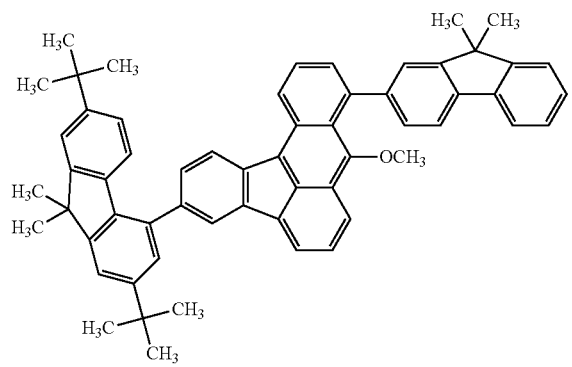
D-14
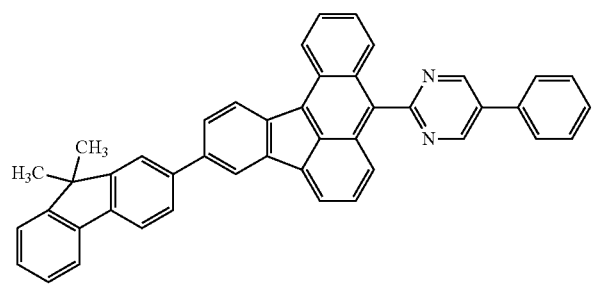
D-15
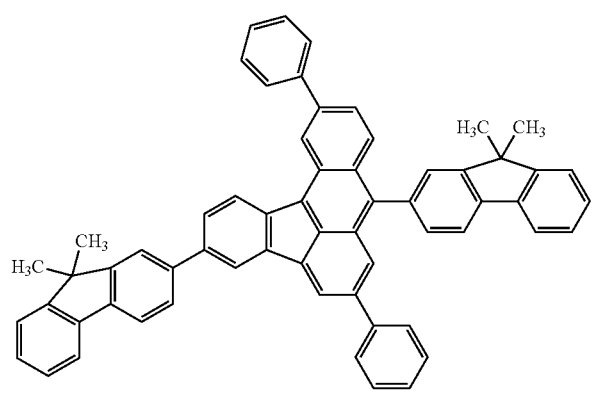
D-16
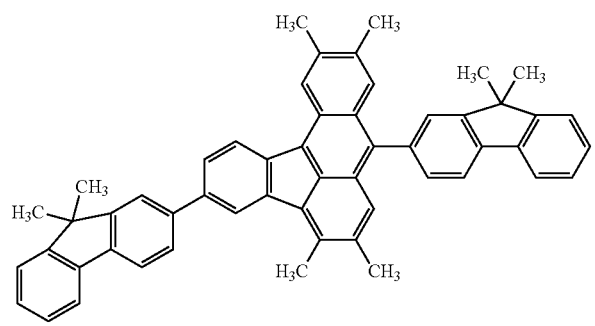
D-17
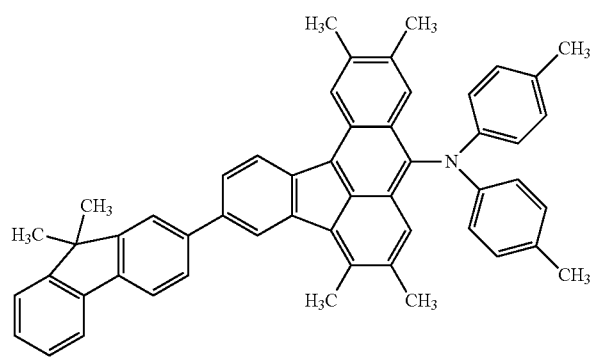
D-18
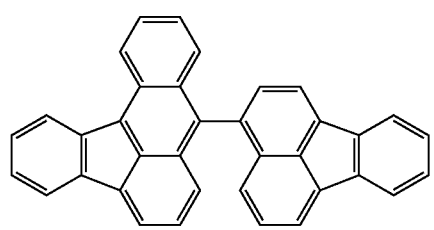
D-19
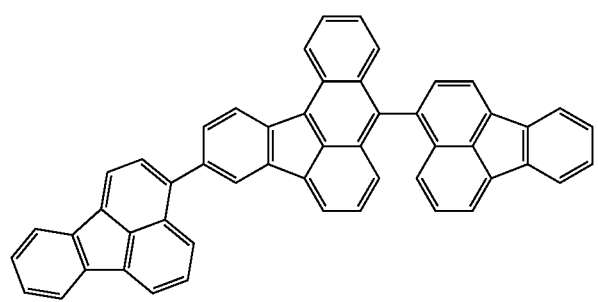
D-20
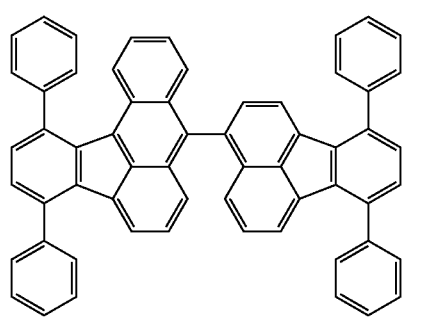

-continued
D-21
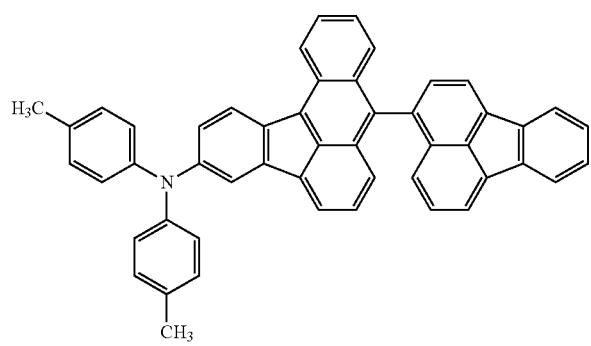
D-22
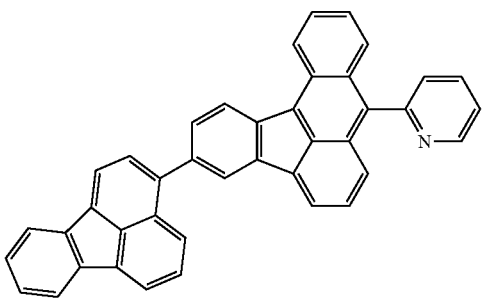
D-23
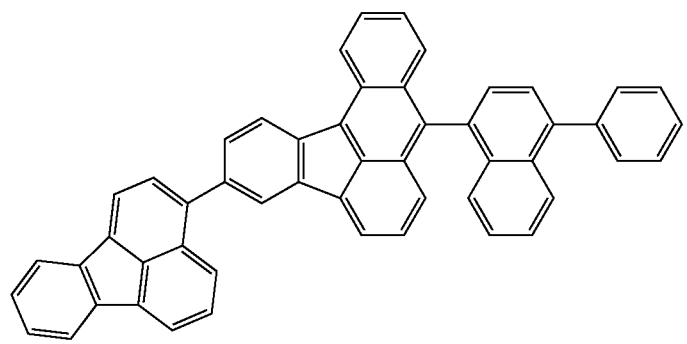
D-24
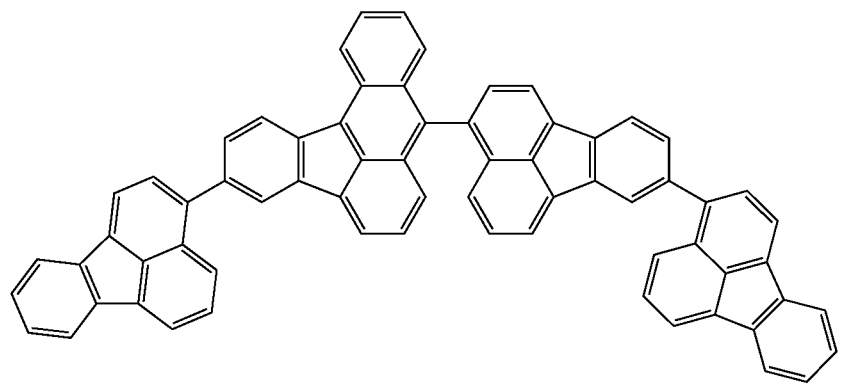
D-25
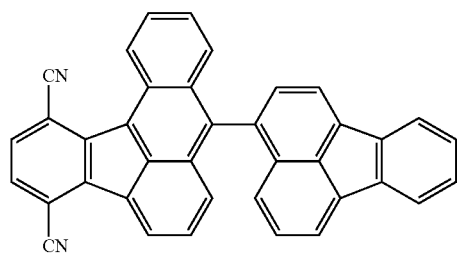
D-26
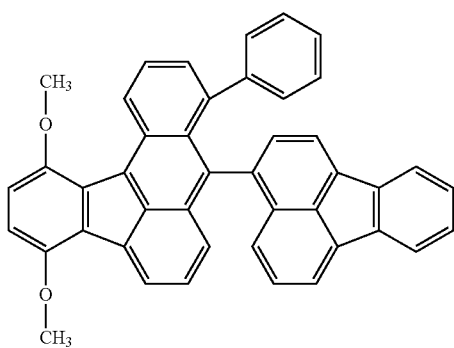

-continued
D-27
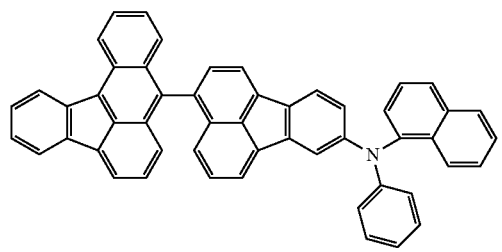
D-28
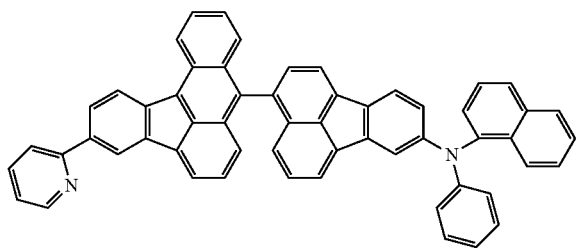
D-29 D-30
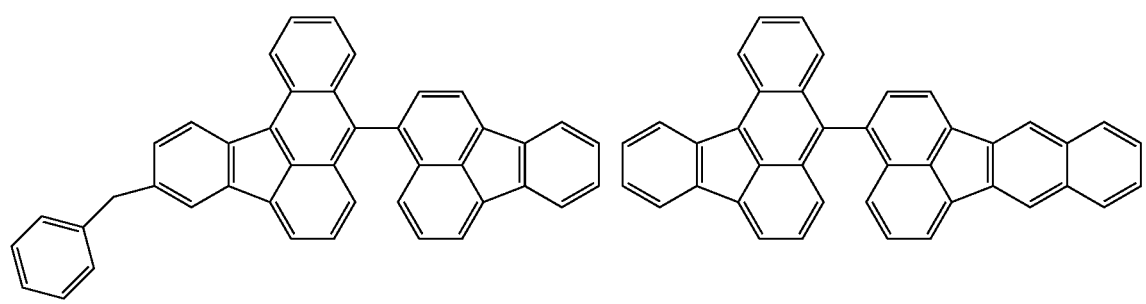
D-31
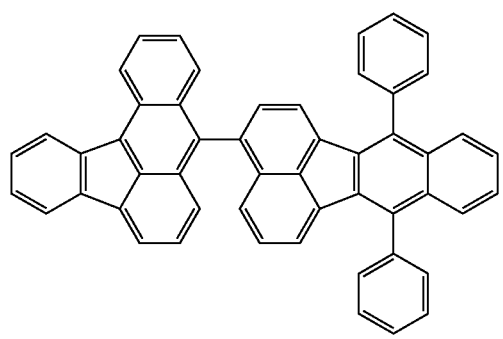
D-32
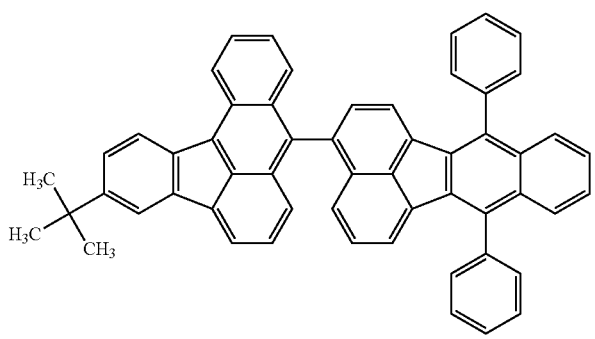
D-33
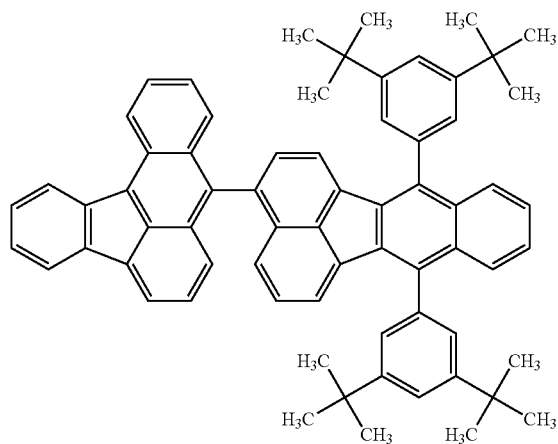
D-34
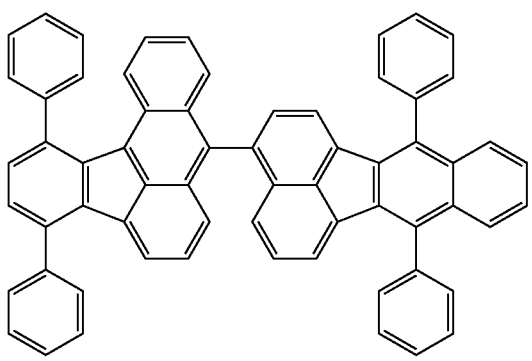

-continued
D-35
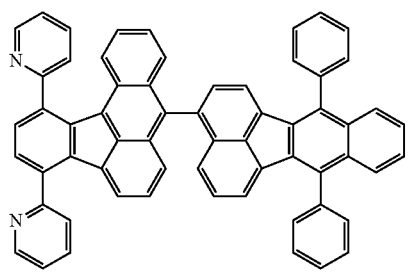
D-36
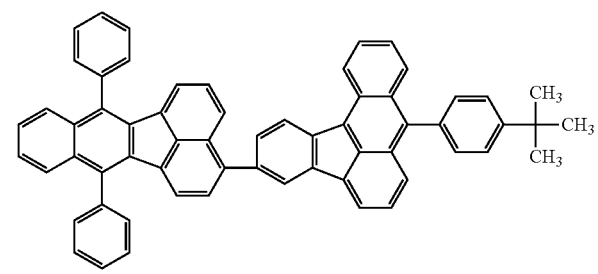
D-37
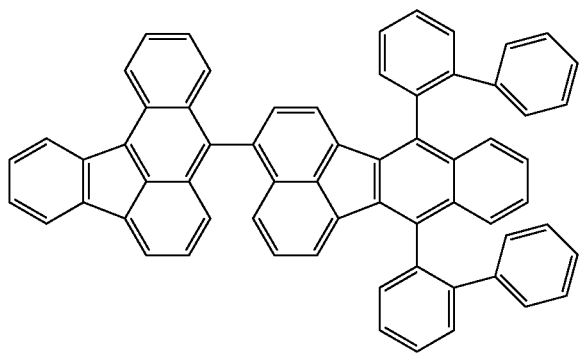
D-38
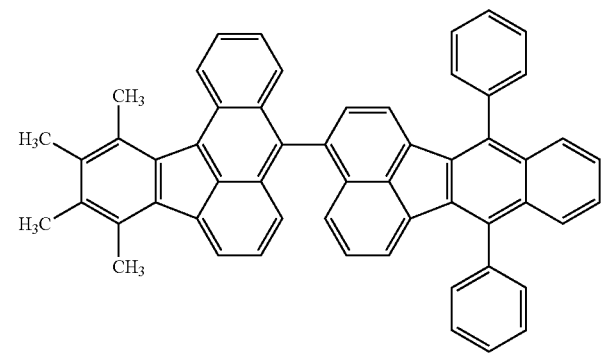
D-39
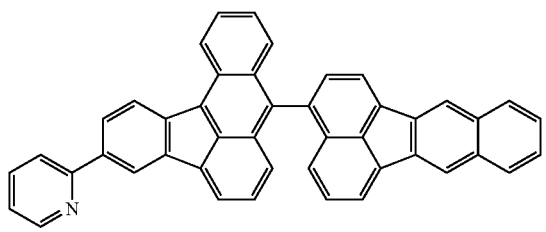
D-40
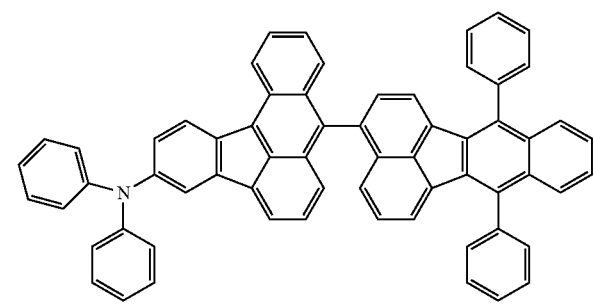
D-41
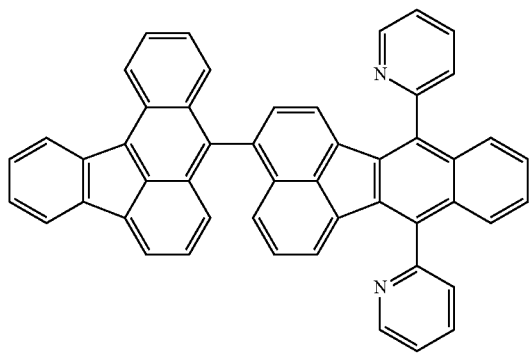
D-42
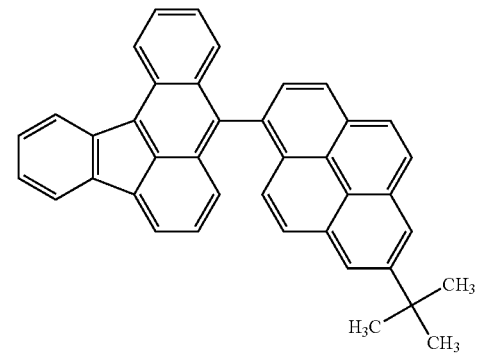

-continued
D-43
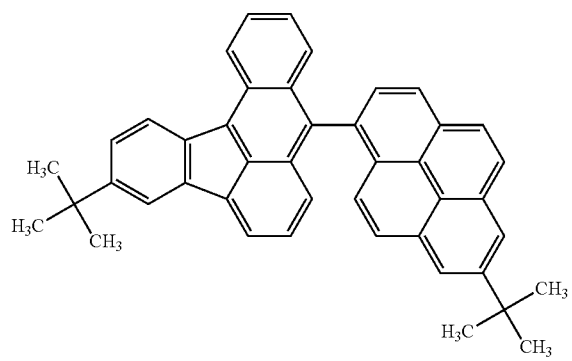
D-44
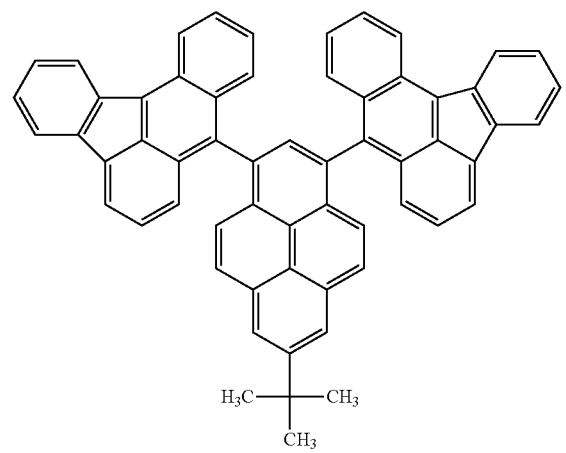
D-45
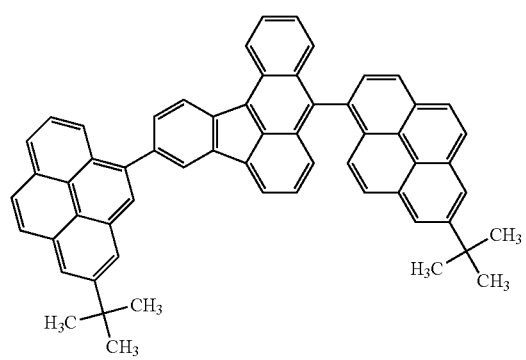
D-46
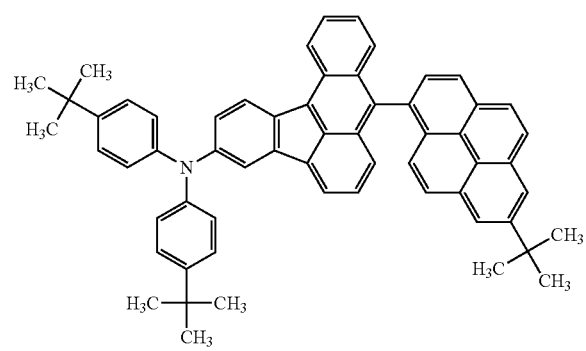
D-47
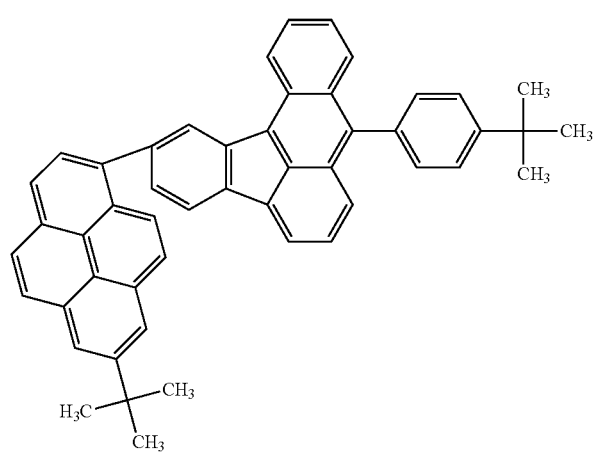
D-48
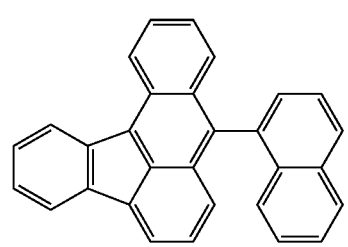
D-49
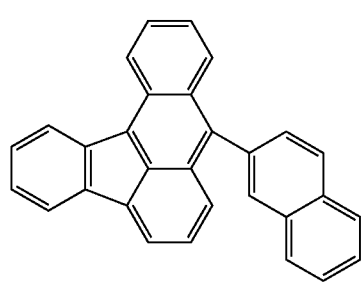

The benzo[a]fluoranthene compound of the present invention can be used as a material of which an organic light emitting device is formed. In addition, the incorporation of the benzo[a]fluoranthene compound of the present invention as a component for the organic light emitting device improves the light emitting efficiency, color purity, and durability of the organic light emitting device. The reason why those properties are improved will be described below.

The benzo[a]fluoranthene compound of the present invention contains a five-membered ring structure. Here, the benzo[a]fluoranthene compound of the present invention is provided with electron injecting property by virtue of electron withdrawing property resulting from the five-membered ring structure. Accordingly, the use of the benzo[a]fluoranthene compound of the present invention as a material of which the organic light emitting device is formed can reduce the voltage at which the device is driven because the use allows an electron generated from a cathode to be efficiently transported. As a result, the light emitting efficiency of the organic light emitting device can be improved. In addition, the use contributes also to the lengthening of the lifetime of the organic light emitting device.

In addition, the introduction of a substituent into the benzo[a]fluoranthene compound of the present invention can appropriately adjust the levels of the HOMO and LUMO of the compound. Accordingly, a molecule of the compound can be designed while a balance between the amount in which a hole as a carrier is injected and the amount in which an electron as another carrier is injected is taken into consideration.

According to J. Phys. Chem. 1994, 98, 5639-5643, an improvement in color purity of light emitted from an organic light emitting device requires a light emitting material of which the device is formed to satisfy the following requests:
1. a molecule of the light emitting material shows a small Stokes shift (a change in structure of the molecule in an excited state as compared to the structure of the molecule in a ground state is small);
2. the association of the molecules of the light emitting material is suppressed; and
3. the emission spectrum of a molecule of the light emitting material has a narrow half width.

Here, in particular, a fluorenyl group, a benzofluoranthenyl group, a fluoranthenyl group, a pyrenyl group, a perylenyl group, or the like as a substituent to be introduced into the benzo[a]fluoranthene compound of the present invention shows a small Stokes shift.

In addition, as described above, the benzo[a]fluoranthene compound of the present invention has a substituent having large steric hindrance, so the association of the molecules of the compound is suppressed.

Further, in the benzo[a]fluoranthene compound of the present invention, the introduction of a substituent showing a small Stokes shift or having a small number of rotating sites can narrow the half width of the emission spectrum of a molecule of the light emitting material. To be specific, in the benzo[a]fluoranthene compound of the present invention, the introduction of a fluorene group can narrow the half width of the emission spectrum to a larger extent than that in the case of the introduction of a biphenyl group because the fluorene group has a smaller number of rotating sites than that of the biphenyl group, and shows a smaller Stokes shift than that of the biphenyl group. Therefore, the use of the benzo[a]fluoranthene compound of the present invention as a light emitting material can improve the color purity of light emitted from an organic light emitting device. To be specific, when, for example, a fluorenyl group, a benzofluoranthenyl group, a fluoranthenyl group, a pyrenyl group, or a perylenyl group is used as a substituent, the substituent shows a small Stokes shift.

In addition, a molecule of the benzo[a]fluoranthene compound of the present invention can be designed in correspondence with a desired luminescent color because any one of various substituents can be introduced into the compound.

The chemical stability of a material of which an organic light emitting device is formed is an important factor for the durability of the device.

The benzo[a]fluoranthene compound of the present invention is chemically stable because the compound shows low reactivity against the electrophilic reaction of a singlet oxygen molecule or the like by virtue of an electron withdrawing effect originating from the five-membered ring structure.

Here, the substituent formed of a carbon atom and a hydrogen atom is preferably introduced into the position of $R_{15}$ in the benzo[a]fluoranthene compound of the formula (I). Since the position is the substitution position at which electrophilic reactivity is highest in the benzo[a]fluoranthene skeleton, the introduction of a substituent having a lower elimination ability and lower chemical reactivity than those of a hydrogen atom into the position additionally improves the chemical stability of the benzo[a]fluoranthene compound.

A sterically bulky fused polycyclic group among aryl group and heterocyclic group is more preferably introduced into the position of $R_{15}$ of the formula (I). In this case, the chemical stability of the compound itself is additionally improved by a reducing effect of the steric hindrance of the substituent on the chemical reactivity of the compound.

On the other hand, when a substituent by which the benzo[a]fluoranthene skeleton is substituted has a wider band gap than that of benzo[a]fluoranthene, light emission originating from the substituent becomes dominant in the light emission of a molecule itself of the compound. This is because the HOMO or LUMO of the compound is localized in the benzo[a]fluoranthene skeleton. In this case, the durability of the organic light emitting device is improved because the effect of the chemical stability of the benzo[a]fluoranthene skeleton is additionally improved.

Next, an organic light emitting device of the present invention will be described in detail.

The organic light emitting device of the present invention includes an anode, a cathode, and a layer including an organic compound, the layer being interposed between the anode and cathode. In addition, the layer including an organic layer contains at least one kind of a benzo[a]fluoranthene compound of the present invention.

Hereinafter, an organic light emitting device of the present invention will be described in detail with reference to the drawings.

First, the symbols will be described.

Reference numeral 1 denotes a substrate; 2, an anode; 3, a light emitting layer; 4, a cathode; 5, a hole transporting layer; 6, an electron transporting layer; 7, a hole injecting layer; 8, a hole/exciton blocking layer; and 10, 20, 30, 40, and 50 each denote an organic light emitting device.

FIG. 1 is a cross sectional view illustrating an organic light emitting device according to a first embodiment of the present invention. The organic light emitting device 10 of FIG. 1 includes the anode 2, the organic light emitting layer 3, and the cathode 4, which are sequentially formed on the substrate 1. The organic light emitting device 10 is useful in a case where the light emitting layer 3 is formed of a compound which has all the properties including a hole transporting ability, an electron transporting ability, and light emitting property or a case where the light emitting layer 3 is formed of a mixture of compounds each having one of the hole transporting ability, the electron transporting ability, and the light emitting property.

Figure 2:
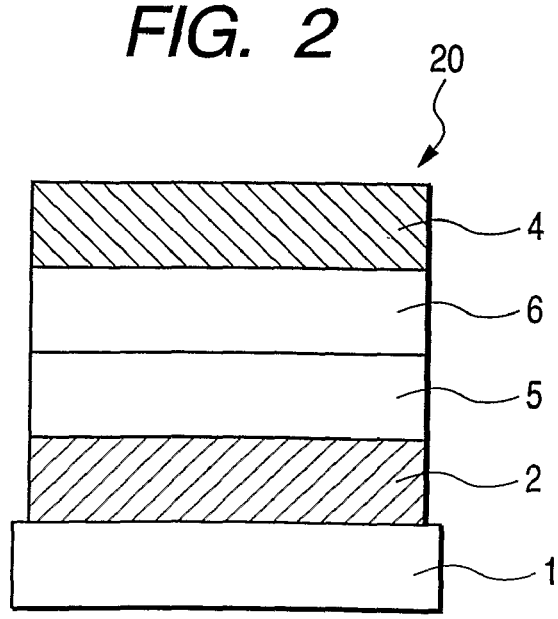
FIG. 2 is a cross sectional view illustrating an organic light emitting device according to a second embodiment of the present invention.

FIG. 2 is a cross sectional view illustrating the organic light emitting device according to a second embodiment of the present invention. The organic light emitting device 20 of FIG. 2 includes the anode 2, the hole transporting layer 5, the electron transporting layer 6, and the cathode 4, which are sequentially formed on the substrate 1. The organic light emitting device 20 is useful in a case where a light emitting organic compound having one of hole transporting property and electron transporting property and an organic compound having electron transporting property alone or hole transporting property alone are used in combination. In addition, in the light emitting device 20, the hole transporting layer 5 or the electron transporting layer 6 serves as the light emitting layer.

Figure 3:
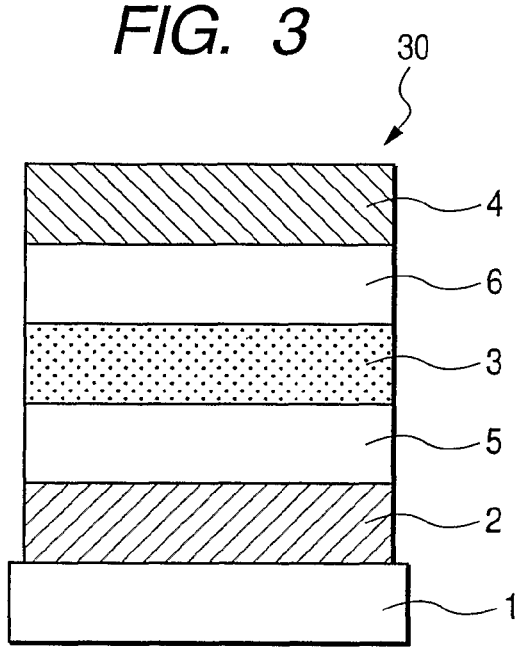
FIG. 3 is a cross sectional view illustrating an organic light emitting device according to a third embodiment of the present invention.

FIG. 3 is a cross sectional view illustrating the organic light emitting device according to a third embodiment of the present invention. The organic light emitting device 30 of FIG. 3 illustrate a structure in which the light emitting layer 3 is inserted between the hole transporting layer 5 and the electron transport layer 6 in the organic light emitting device 20 of FIG. 2. In the organic light emitting device 30, a carrier transporting function and a light emitting function are separated from each other. Thus, the device can be used appropriately in combination with organic compounds each having one of the hole transporting property, electron transporting property, and light emitting property. Therefore, the degree of freedom in selection of a material extremely increases as well as various compounds different from each other in emission wavelength can be used. As a result, the range of luminescent colors can be widened. Further, a light emitting efficiency of the organic light emitting device 30 can be improved by effectively trapping carrier or exciton in the central light emitting layer 3.

Figure 4:
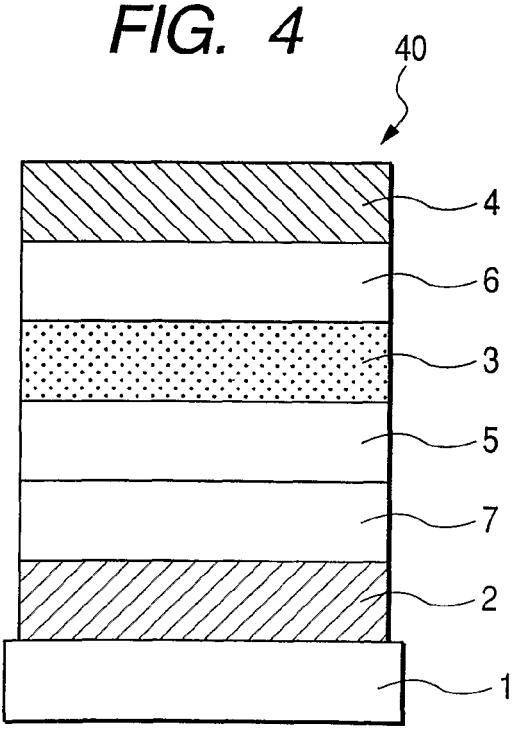
FIG. 4 is a cross sectional view illustrating an organic light emitting device according to a fourth embodiment of the present invention.

FIG. 4 is a cross sectional view illustrating the organic light emitting device according to a fourth embodiment of the present invention. The organic light emitting device 40 of FIG. 4 illustrate a structure in which the hole injecting layer 7 is provided between the anode 2 and the hole transporting layer 5 in the organic light emitting device 30 of FIG. 3. The provision of the hole injecting layer 7 in the organic light emitting device 40 imparts an improving effect on adhesiveness between the anode 2 and the hole transporting layer 5 or on hole injection property, and is effective for a reduction in voltage at which the device is driven.

Figure 5:
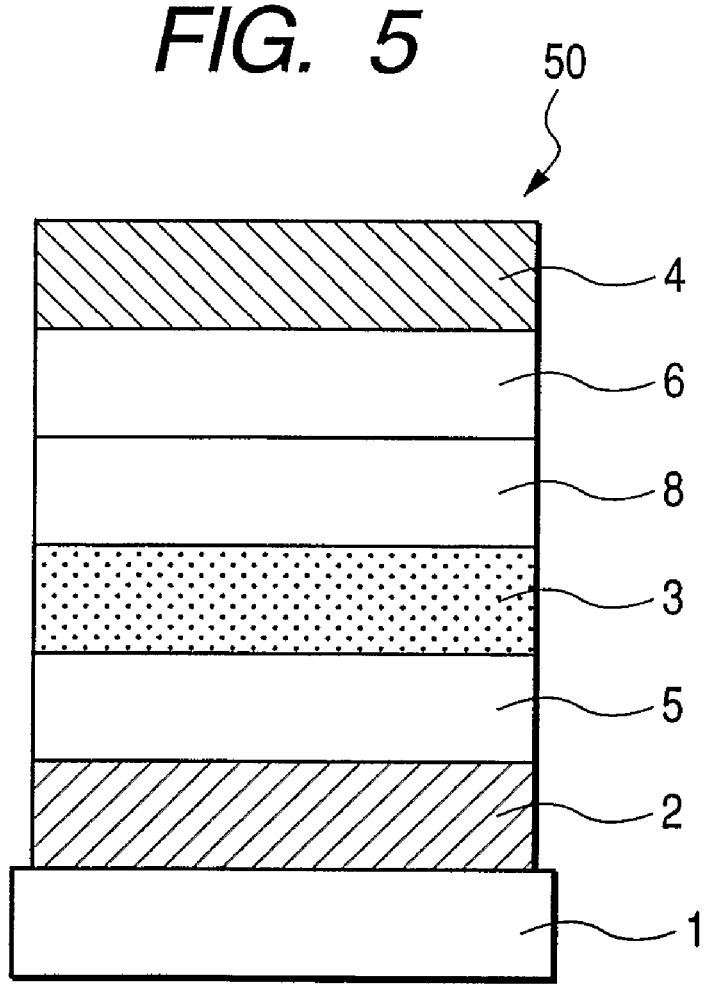
FIG. 5 is a cross sectional view illustrating an organic light emitting device according to a fifth embodiment of the present invention.

FIG. 5 is a cross sectional view illustrating the organic light emitting device according to a fifth embodiment of the present invention. The organic light emitting device 50 of FIG. 5 illustrate a structure in which a layer for inhibiting the escape of a hole or exciton toward the side of the cathode 4 (hole/exciton blocking layer 8) is inserted between the light emitting layer 3 and the electron transporting layer 6 in the organic light emitting device 30 of FIG. 3. The use of a compound having an extremely high ionization potential as the hole/exciton blocking layer 8 improves the light emitting efficiency of the organic light emitting device 50.

It should be noted that the device structures according to the first to fifth embodiments are each merely very basic one, and the structure of the organic light emitting device using the benzo[a]fluoranthene compound of the present invention is not limited to those. For example, an insulating layer may be provided onto an interface between an electrode and an organic layer, an adhesive layer or an interference layer may be provided thereonto, and a hole transporting layer may be formed of two layers having different ionization potentials.

The benzo[a]fluoranthene compound of the present invention can be used in any one of the above-mentioned first to fifth embodiments.

The benzo[a]fluoranthene compound of the present invention can be used as a material for an organic light emitting device. To be specific, the compound can be used as a material of which each of the hole transporting layer, electron transporting layer, and light emitting layer of the device is formed. In this case, one benzo[a]fluoranthene compound of the above kind may be used, or multiple benzo[a]fluoranthene compounds of the above kind may be used. Alternatively, the benzo[a]fluoranthene compound may be incorporated into each of multiple layers. The use of the benzo[a]fluoranthene compound of the present invention improves the light emitting efficiency and lifetime of the organic light emitting device.

The benzo[a]fluoranthene compound of the present invention is particularly preferably used as a material of which the light emitting layer is formed not only because the compound can be used in any one of various embodiments but also because the performance of the organic light emitting device can be improved in terms of color purity, light emitting efficiency, and lifetime.

The light emitting layer may be formed only of the benzo[a]fluoranthene compound of the present invention. Alternatively, the light emitting layer may be formed of a host and a guest. Here, the benzo[a]fluoranthene compound of the present invention can be used in any one of a dopant material serving as a guest, and a fluorescent material and a phosphorescent material each serving as a host. The use of the benzo[a]fluoranthene compound of the present invention as a host or guest in the light emitting layer can improve the performance of the organic light emitting device in terms of color purity, light emitting efficiency, and lifetime.

When the benzo[a]fluoranthene compound of the present invention is used as a guest for the light emitting layer, the corresponding host, which is not particularly limited, is preferably a fused polycyclic derivative from the following viewpoint: an organic light emitting device formed of a stable amorphous film should be provided. Here, in order that an organic light emitting device having high efficiency and durability may be provided, the emission quantum yield of the host itself must be high, and the host itself must be chemically stable. A preferable fused polycyclic derivative satisfying those requests is, for example, a fluorene derivative, a pyrene derivative, a fluoranthene derivative, or a benzofluoranthene derivative. Each of those derivatives has a high emission quantum yield, and is chemically stable.

Here, when the benzo[a]fluoranthene compound of the present invention is used as a guest for the light emitting layer, the content of the compound is preferably 0.1 wt % or more to 30 wt % or less with respect to the total weight of the materials of which the light emitting layer is formed; the content is more preferably 0.1 wt % or more to 15 wt % or less from the viewpoint of the suppression of concentration quenching.

On the other hand, when the benzo[a]fluoranthene compound of the present invention is used as a host for the light emitting layer, the corresponding guest is not particularly limited, and can be appropriately selected depending on, for example, a desired luminescent color. In addition, a hole transportable compound, an electron transportable compound, or the like as well as the guest can be used as required by doping the layer with such compound together with the guest.

The organic light emitting device of the present invention uses the benzo[a]fluoranthene compound of the present invention particularly as a material of which the light emitting layer of the device is formed. In addition, the organic light emitting device of the present invention can use, for example, any one of the conventionally known low-molecular-weight-based and polymer-based hole transportable compounds, luminous compounds, and electron transportable compounds together with the benzo[a]fluoranthene compound of the present invention as required.

Examples of the hole transportable compounds include triarylamine derivatives, aryldiamine derivatives, phthalocyanine derivatives, porphyrin derivatives, poly(vinylcarbazole), poly(silylene), poly(thiophene), and other conductive polymers.

Examples of the light emitting compound other than the benzo[a]fluoranthene compound of the present invention include: fused ring aromatic compounds (including naphthalene derivatives, phenanthrene derivatives, fluorene derivatives, pyrene derivatives, tetracene derivatives, coronene derivatives, chrysene derivatives, perylene derivatives, 9,10-diphenylanthracene derivatives, and rubrene); quinacridone derivatives; acridone derivatives; coumarin derivatives; pyran derivatives; Nile red; pyrazine derivatives; benzoimidazole derivatives; benzothiazole derivatives; benzoxazole derivatives; stilbene derivatives; organometallic complexes (including organic aluminum complexes such as tris(8-quinolinolato)aluminum, and organic beryllium complexes); and high-molecular derivatives such as poly(phenylene vinylene) derivatives, poly(fluorene) derivatives, poly(phenylene) derivatives, poly(thienylene vinylene) derivatives, and poly (acetylene) derivatives.

Examples of the electron transportable compound include oxadiazole derivatives, oxazole derivatives, thiazole derivatives, thiadiazole derivatives, pyrazine derivatives, triazole derivatives, triazine derivatives, perylene derivatives, quinoline derivatives, quinoxaline derivatives, fluorenone derivatives, anthrone derivatives, phenanthroline derivatives, and organometallic complexes.

A desirable anode material has as large a work function as possible. Examples of available anode include: metal elements such as gold, platinum, silver, copper, nickel, palladium, cobalt, selenium, vanadium, and tungsten, and alloys thereof; and metal oxides such as tin oxide, zinc oxide, indium oxide, indium tin oxide (ITO), and indium zinc oxide. Further, conductive polymers such as polyaniline, polypyrrole, polythiophene, and polyphenylene sulfide may also be used. Each of those electrode substances may be used singly. Alternatively, two or more of them may also be used in combination. Further, the anode may be formed of a single layer and may be formed of multiple layers.

A desirable cathode material has as small a work function as possible. Examples of available cathode include: metal elements such as lithium, sodium, potassium, calcium, magnesium, aluminum, indium, ruthenium, titanium, manganese, yttrium, silver, lead, tin, and chromium. Alternatively, those metal elements may be used in combination as alloys. For example, the following alloys can be used: lithium-indium, sodium-potassium, magnesium-silver, aluminum-lithium, aluminum-magnesium, and magnesium-indium alloys. Further, metal oxides such as indium tin oxide (ITO) may also be used. Each of those electrode substances may be used singly or in combination of two or more. Further, the cathode may be formed of a single layer and may be formed of multiple layers.

Substrates which may be used in the present invention include: opaque substrates such as metallic substrates and ceramics substrates; and transparent substrates such as glass, quartz, and plastic sheet substrates, but are not particularly limited to these materials.

In addition, a color filter film, a fluorescent color converting film, a dielectric reflection film, or the like may be used in the substrate to control emitted light. The device of the present invention can also be produced by being connected to a thin-film transistor (TFT) produced on a substrate.

Moreover, with respect to a direction of extracting light of the device, both a bottom emission structure (structure in which light is extracted from the substrate side) and a top emission structure (structure in which light is extracted from a side opposite to the substrate) can be acceptable.

The organic light emitting device of the present invention is produced by a method such as a vacuum vapor deposition method, a solution application method, a transfer method involving the use of laser or the like, or a spray method. Here, an organic layer containing the benzo[a]fluoranthene compound of the present invention is preferably formed by, for example, the vacuum vapor deposition method or the solution application method because the crystallization or the like of the layer itself to be formed hardly occurs, and the layer is excellent in stability over time.

Hereinafter, the present invention will be further specifically described with reference to Examples, but is not limited thereto.

Example 1

Synthesis of Exemplified Compound D-31

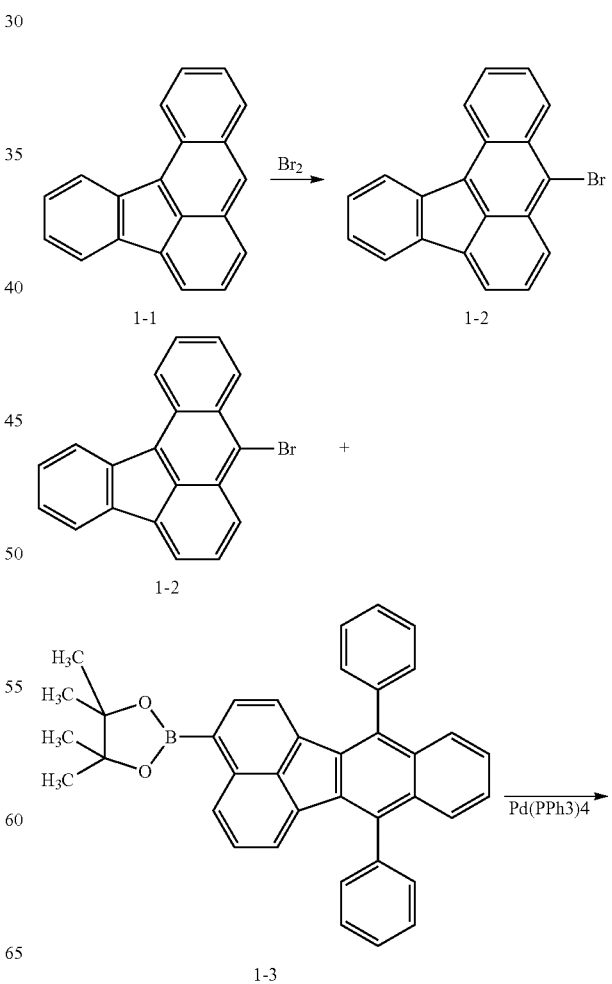

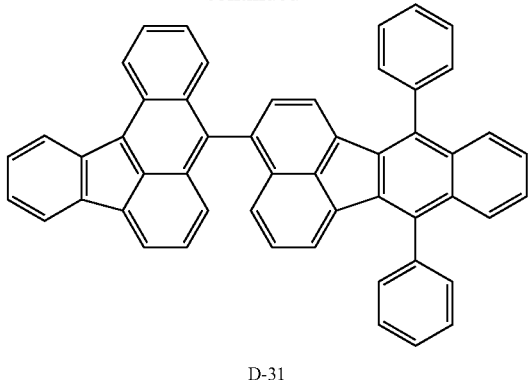

D-31

(a) Synthesis of Intermediate Compound 1-2

A reagent and a solvent shown below were loaded into a 200-ml three-necked flask.
Compound 1-1: 1.0 g (3.96 mmol)
Dichloromethane: 50 ml Next, a solution prepared by mixing 0.20 ml of bromine and 10 ml of dichloromethane was dropped to the mixture while the mixture was stirred under a nitrogen atmosphere and under ice cooling. Next, the reaction solution was stirred for 5 hours. After the completion of the reaction, the reaction solution was filtrated, and the resultant crystal was washed with methanol, whereby 1.24 g of Intermediate 1-2 as a yellow crystal were obtained (95% yield).

(b) Synthesis of Exemplified Compound D-31

Reagents and solvents shown below were loaded into a 200-ml three-necked flask.
Compound 1-2: 0.205 g (0.623 mmol)
Compound 1-3: 0.220 g (0.415 mmol)
Toluene: 50 ml
Ethanol: 20 ml Next, an aqueous solution prepared by mixing 5 g of cesium carbonate and 50 ml of water was dropped to the reaction solution while the reaction solution was stirred under a nitrogen atmosphere at room temperature. Subsequently, 0.100 g of tetrakis(triphenylphosphine)palladium(0) was added to the reaction solution. Next, the temperature of the reaction solution was increased to 77° C., and the reaction solution was stirred for 5 hours. After the completion of the reaction, the organic layer was extracted with toluene and dried with anhydrous sodium sulfate, and then the solvent was removed by distillation under reduced pressure. Next, the remainder was purified by silica gel column chromatography (developing solvent: a mixed solvent of toluene and heptane), whereby 0.231 g of Exemplified Compound D-31 as a yellow crystal was obtained (85% yield).

Mass spectrometry confirmed that Exemplified Compound D-31 had an M+ of 655.

In addition, $^1$H-NMR measurement identified the structure of Exemplified Compound D-31.

$^1$H-NMR (CDCl$_3$, 400 MHz) σ(ppm): 8.84 (d, 1H), 8.44 (d, 1H), 8.02 (d, 1H), 7.98-7.96 (m, 1H), 7.73-7.58 (m, 14H), 7.52-7.48 (t, 1H), 7.44-7.39 (m, 6H), 7.28-7.24 (m, 1H), 7.10-7.06 (t, 1H), 6.98 (d, 1H), 6.80 (d, 1H), 6.60 (d, 1H)

In addition, an emission spectrum in a dilute solution of Exemplified Compound D-31 in toluene having a concentration of 10$^{-6}$ mol/l was measured. As a result, the emission spectrum showed a good green color having an emission peak at 513 nm. It should be noted that the emission spectrum was measured with a fluorophotometer (F-4500 manufactured by Hitachi, Ltd.) at an excitation wavelength of 340 nm.

Exemplified Compound D-31 was evaluated for its emission quantum yield by the following method.

To be specific, first, a dilute solution of Exemplified Compound D-31 in toluene having a concentration of 10$^{-6}$ mol/l was prepared. Next, the absorbance of the dilute solution at a wavelength of 340 nm was measured with a spectrophotometer (U-3310 manufactured by Hitachi, Ltd.).

Next, the emission spectrum of the dilute solution when a wavelength of 340 nm was defined as an excitation wavelength was measured with a fluorophotometer (F-4500 manufactured by Hitachi, Ltd.), and the area of an emission peak was calculated from the resultant emission spectrum.

A relative value for the emission quantum yield of the compound when a value for diphenylanthracene was set to 1.0 was calculated by using the absorbance and the area of the emission peak described above, and was defined as Relative Quantum Yield 1. Meanwhile, a relative value for the emission quantum yield of the compound when a value for benzo[a]fluoranthene was set to 1.0 was similarly calculated, and was defined as Relative Quantum Yield 2. Table 3 shows the results of the calculation of Relative Quantum Yield 1 and Relative Quantum Yield 2 in Exemplified Compound D-31.

Examples 2 to 6

Synthesis of Exemplified Compounds D-2, D-3, D-6, D-48, and D-49

Each of Exemplified Compounds D-2, D-3, D-6, D-48, and D-49 can be synthesized by using the corresponding one of the pinacolborane derivatives shown in Table 2 below instead of Compound 1-3 in the section (b) of Example 1. It should be noted that the $^1$H-NMR spectra of Exemplified Compounds D-2, D-3, D-6, D-48, and D-49 are as shown below.

Example Compound D-2: $^1$H-NMR (CDCl$_3$, 400 MHz) σ(ppm): 8.87 (d, 1H), 8.45 (d, 1H), 8.08-8.03 (m, 3H), 7.97-7.91 (m, 2H), 7.83-7.67 (m, 8H), 7.62-7.57 (m, 2H), 7.53-7.32 (m, 7H), 1.65 (s, 6H), 1.59 (s, 6H)

Example Compound D-3: $^1$H-NMR (CDCl$_3$, 400 MHz) σ(ppm): 8.80 (d, 2H), 8.47 (d, 2H), 8.11-8.06 (m, 8H), 7.81 (d, 2H), 7.73-7.42 (m, 14H), 1.66 (s, 6H)

Example Compound D-6: $^1$H-NMR (CDCl$_3$, 400 MHz) σ(ppm): 8.87 (d, 1H), 8.46 (d, 1H), 8.07-8.01 (m, 3H), 7.92 (d, 1H), 7.84 (d, 1H), 7.74 (d, 1H), 7.70-7.68 (m, 1H), 7.60-7.57 (t, 1H), 7.54-7.49 (m, 3H), 7.45-7.38 (m, 5H), 2.10-2.06 (m, 4H), 0.48-0.45 (m, 3H)

Example Compound D-48: $^1$H-NMR (CDCl$_3$, 400 MHz) σ(ppm): 8.88 (d, 1H), 8.48 (d, 1H), 8.06 (t, 1H), 8.01 (t, 1H), 7.70 (t, 1H), 7.66 (t, 1H), 7.63 (d, 1H), 7.60 (d, 1H), 7.53 (t, 1H), 7.49-7.43 (m, 3H), 7.39 (d, 1H), 7.31 (t, 1H), 7.21 (t, 1H), 7.15 (d, 1H)

Example Compound D-49: $^1$H-NMR (CDCl$_3$, 400 MHz) σ(ppm): 8.88 (d, 1H), 8.47 (d, 1H), 8.07-8.02 (m, 5H), 7.97-7.93 (m, 2H), 7.71-7.65 (m, 3H), 7.62-7.60 (m, 2H), 7.57-7.51 (m, 2H), 7.45-7.40 (m, 2H)

In addition, an emission spectrum in a dilute solution of each of Exemplified Compounds D-2, D-3, D-6, D-48, and D-49 in toluene having a concentration of 10$^{-6}$ mol/l was measured in the same manner as in Example 1. Table 2 shows the results.

TABLE 2

| | Benzo[a]fluoranthene derivative | Pinacolborane derivative | Luminous wavelength [nm] |
|---|---|---|---|
| Example 2 | Exemplified Compound D-2 | | 515 |
| Example 3 | Exemplified Compound D-3 | | 513 |
| Example 4 | Exemplified Compound D-6 | | 513 |
| Example 5 | Exemplified Compound D-48 | | 502 |
| Example 6 | Exemplified Compound D-49 | | 508 |

Further, Relative Quantum Efficiency 1 and Relative Quantum Efficiency 2 were calculated for each of Exemplified Compounds D-2, D-3, and D-6 in the same manner as in Example 1. Table 3 shows the results of the calculation.

Comparative Example 1

A dilute solution of Compound 2-1 shown below in toluene having a concentration of $10^{-6}$ mol/l was prepared.

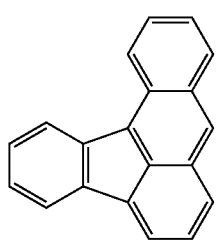

2-1

The absorption spectrum and emission spectrum of the dilute solution in toluene were each measured in the same manner as in Example 1. In addition, Relative Quantum Yield 1 and Relative Quantum Yield 2 were each calculated from the resultant absorption spectrum and the resultant emission spectrum in the same manner as in Example 1. Table 3 shows the results of the calculation.

Comparative Example 2

A dilute solution of Compound 2-2 shown below in toluene having a concentration of $10^{-6}$ mol/l was prepared.

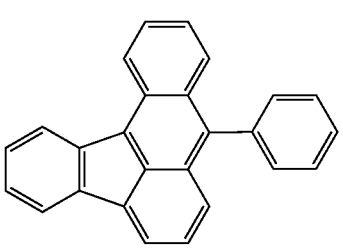

2-2

The absorption spectrum and emission spectrum of the dilute solution in toluene were each measured in the same manner as in Example 1. In addition, Relative Quantum Yield 1 and Relative Quantum Yield 2 were each calculated from the resultant absorption spectrum and the resultant emission spectrum in the same manner as in Example 1. Table 3 shows the results of the calculation.

TABLE 3

| | Compound No. | Relative Quantum Efficiency 1 | Relative Quantum Efficiency 2 |
|---|---|---|---|
| Example 1 | Exemplified Compound D-31 | 0.37 | 1.94 |
| Example 2 | Exemplified Compound D-2 | 0.41 | 2.15 |
| Example 3 | Exemplified Compound D-3 | 0.37 | 1.94 |
| Example 4 | Exemplified Compound D-6 | 0.34 | 1.78 |
| Comparative Example 1 | 2-1 | 0.19 | 1.0 |
| Comparative Example 2 | 2-2 | 0.23 | 1.21 |

Example 5

Synthesis of Exemplified Compound D-9

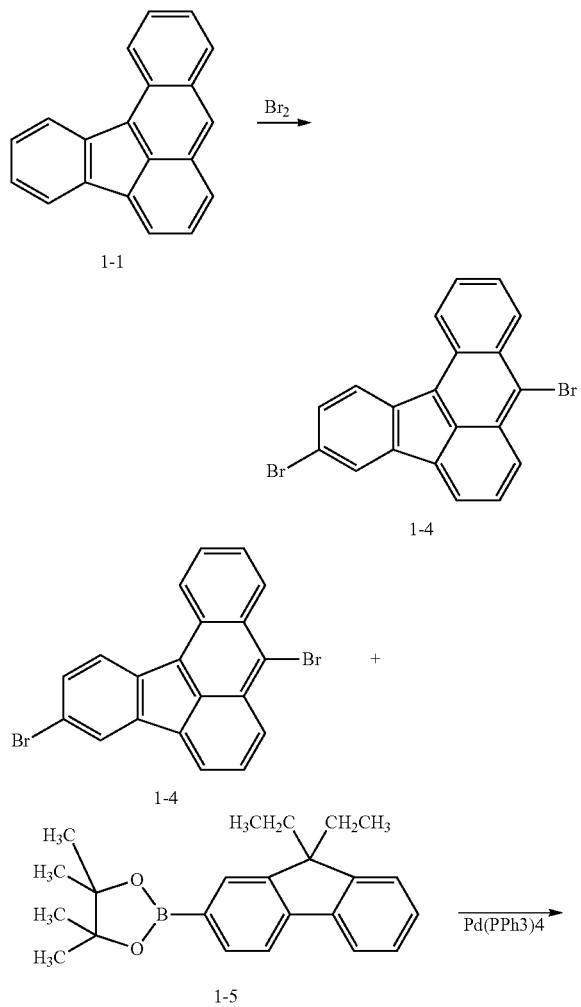

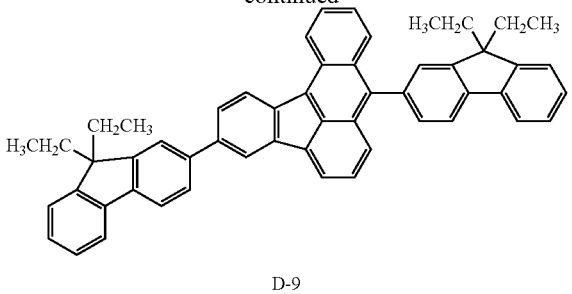

D-9

(a) Synthesis of Intermediate Compound 1-4

A reagent and a solvent shown below were loaded into a 200-ml three-necked flask.
Compound 1-1: 1.0 g (3.96 mmol)
Dichloromethane: 50 ml Next, a solution prepared by mixing 0.40 ml of bromine and 10 ml of dichloromethane was dropped to the mixture while the reaction solution was stirred under a nitrogen atmosphere and under ice cooling, and the reaction solution was stirred for 5 hours. After the completion of the reaction, the reaction solution was filtrated, and the resultant crystal was washed with methanol, whereby 1.46 g of Intermediate 1-4 as a yellow crystal were obtained (90% yield).

(b) Synthesis of Exemplified Compound D-9

Reagents and solvents shown below were loaded into a 200-ml three-necked flask.
Compound 1-4: 0.255 g (0.623 mmol)
Compound 1-5: 0.626 g (1.80 mmol)
Toluene: 50 ml
Ethanol: 20 ml Next, an aqueous solution prepared by mixing 5 g of cesium carbonate and 50 ml of water was dropped to the reaction solution while the reaction solution was stirred under a nitrogen atmosphere at room temperature. Subsequently, 0.150 g of tetrakis(triphenylphosphine)palladium(0) was added to the reaction solution. Next, the temperature of the reaction solution was increased to 77° C., and the reaction solution was stirred for 5 hours. After the completion of the reaction, the organic layer was extracted with toluene and dried with anhydrous sodium sulfate, and then the solvent was removed by distillation under reduced pressure. Next, the remainder was purified by silica gel column chromatography (developing solvent: a mixed solvent of toluene and heptane), whereby 0.323 g of Exemplified Compound D-9 as an orange crystal was obtained (75% yield).

Mass spectrometry confirmed that Exemplified Compound D-9 had an M+ of 693.

In addition, $^1$H-NMR measurement identified the structure of Exemplified Compound D-9.

$^1$H-NMR (CDCl$_3$, 600 MHz) σ(ppm): 8.90 (d, 1H), 8.52 (d, 1H), 8.35 (s, 1H), 8.16 (d, 1H), 8.04 (d, 1H), 7.94 (d, 1H), 7.85-7.51 (m, 10H), 7.45-7.34 (m, 8H), 2.16-2.08 (m, 8H), 0.49-0.42 (m, 12H)

Example 6

Production of Organic Light Emitting Device

As an anode, a film of tin oxide indium (ITO) having a film thicknesses of 120 nm was formed on a glass substrate by a sputtering method. Next, the obtained substrate thus formed was subjected to ultrasonic cleaning with acetone and isopropyl alcohol (IPA) subsequently. Then, the resultant was washed in boiling IPA, followed by drying. Further, the resultant was subjected to UV/ozone cleaning. The thus-treated glass substrate was used as a transparent conductive supporting substrate.

Next, a 0.1 w % solution of Compound 3-1 shown below in chloroform was formed into a film having a thickness of 20 nm on the transparent conductive supporting substrate by a spin coating method, whereby a hole transporting layer was formed.

Compound 3-1

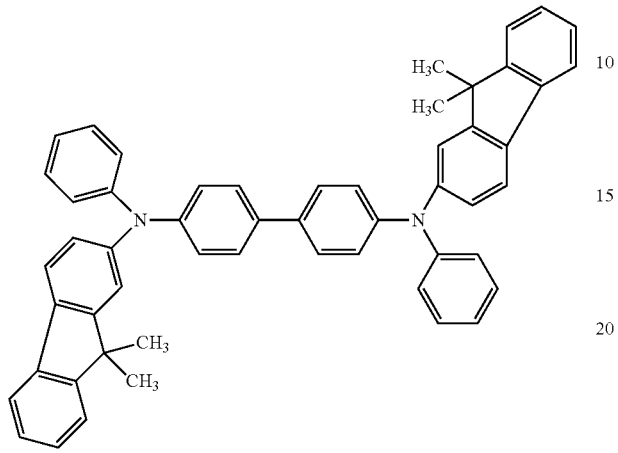

Next, any other organic layer and a layer of which a cathode was formed were continuously formed by a vacuum vapor deposition method based on resistance heating in a vacuum chamber at $10^{-5}$ Pa. To be specific, first, Exemplified Compound D-2 as a guest and Compound 3-2 shown below were co-deposited at a weight concentration ratio of 5:95 so as to serve as a light emitting layer. At that time, the thickness of the light emitting layer was 20 nm. Next, Compound 3-3 shown below was formed into an electron transporting layer having a thickness of 40 nm. Next, LiF was formed into a metal electrode layer 1 having a thickness of 0.5 nm. Next, Al was formed into a metal electrode layer 2 having a thickness of 150 nm. Here, the metal electrode layer 1 and the metal electrode layer 2 each function as a cathode.

Compound 3-2

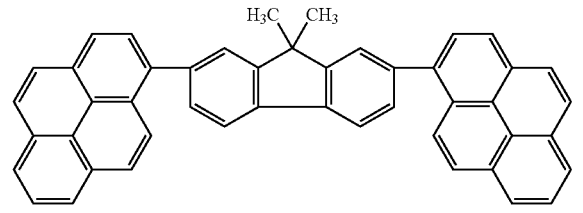

Compound 3-3

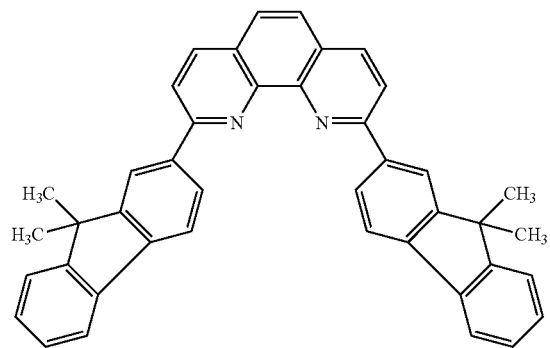

Thus, an organic light emitting device was produced.

A voltage of 6.1 V was applied to the organic light emitting device produced in this example. As a result, the device was observed to emit green light having an emission luminance of 1,720 cd/m² at a current density of 18 mA/cm².

Further, the organic light emitting device of this example was continuously driven for 100 hours under a nitrogen atmosphere while a current density was kept at 165 mA/cm². As a result, the percentage by which the luminance of the device degraded after the driving for 100 hours as compared to the initial luminance of the device was as small as 5% or less.

Example 7

Production of Organic Light Emitting Device

An organic light emitting device was produced in the same manner as in Example 6 except that, in Example 6, Exemplified Compound D-31 was used as a guest for the light emitting layer, and the thickness of the electron transporting layer was changed to 30 nm.

A voltage of 6.1 V was applied to the organic light emitting device produced in this example. As a result, the device was observed to emit green light having an emission luminance of 1,957 cd/m² at a current density of 30 mA/cm².

Further, the organic light emitting device of this example was continuously driven for 100 hours under a nitrogen atmosphere while a current density was kept at 165 mA/cm². As a result, the percentage by which the luminance of the device degraded after the driving for 100 hours as compared to the initial luminance of the device was as small as 1% or less.

Example 8

An organic light emitting device was produced in the same manner as in Example 6 except that, in Example 6, Exemplified Compound D-3 was used as a guest for the light emitting layer.

A voltage of 6.1 V was applied to the organic light emitting device produced in this example. As a result, the device was observed to emit green light having an emission luminance of 1,421 cd/m² at a current density of 18 mA/cm².

Further, the organic light emitting device of this example was continuously driven for 100 hours under a nitrogen atmosphere while a current density was kept at 165 mA/cm². As a result, the percentage by which the luminance of the device degraded after the driving for 100 hours as compared to the initial luminance of the device was as small as 8% or less.

Example 9

An organic light emitting device was produced in the same manner as in Example 6 except that, in Example 6, Exemplified Compound D-48 was used as a guest for the light emitting layer.

A voltage of 6.1 V was applied to the organic light emitting device produced in this example. As a result, the device was observed to emit green light having an emission luminance of 1,205 cd/m² at a current density of 18 mA/cm².

Further, the organic light emitting device of this example was continuously driven for 100 hours under a nitrogen atmosphere while a current density was kept at 165 mA/cm². As a result, the percentage by which the luminance of the device degraded after the driving for 100 hours as compared to the initial luminance of the device was as small as 8% or less.

Example 10

An organic light emitting device was produced in the same manner as in Example 6 except that, in Example 6, Exemplified Compound D-49 was used as a guest for the light emitting layer.

A voltage of 6.1 V was applied to the organic light emitting device produced in this example. As a result, the device was observed to emit green light having an emission luminance of 1,250 cd/m² at a current density of 18 mA/cm².

Further, the organic light emitting device of this example was continuously driven for 100 hours under a nitrogen atmosphere while a current density was kept at 165 mA/cm². As a result, the percentage by which the luminance of the device degraded after the driving for 100 hours as compared to the initial luminance of the device was as small as 8% or less.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-130526, filed May 16, 2007, and Japanese Patent Application No. 2008-095673, filed Apr. 2, 2008, which are hereby incorporated by reference herein in their entirety.

The invention claimed is:

1. A benzo[a]fluoranthene compound represented by the following general formula (I):

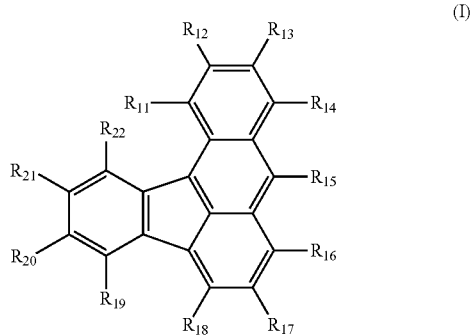

(I)

wherein at least one of $R_{14}$, $R_{15}$, $R_{16}$, $R_{20}$, and $R_{21}$ represents $R_n$, and $R_{11}$ to $R_{22}$ which are not represented by $R_n$ each represent a hydrogen atom, a halogen atom, a substituted or unsubstituted alkyl group, a substituted or unsubstituted alkoxy group, a substituted or unsubstituted aryloxy group, a substituted or unsubstituted alkenyl group, a substituted or unsubstituted alkynyl group, a substituted or unsubstituted aralkyl group, or a substituted or unsubstituted aryl group, and $R_{11}$ to $R_{22}$ which are not represented by $R_n$ may be identical to or different from one another; and wherein $R_n$ is selected from the group consisting of a naphthyl group, a phenanthryl group, a fluorenyl group, a fluoranthenyl group, a benzofluoranthenyl group, a pyrenyl group and perylenyl group.

2. The benzo[a]fluoranthene compound according to claim 1, wherein $R_{15}$ represents $R_n$.

3. An organic light emitting device comprising:

an anode;

a cathode; and a layer including an organic compound, the layer being interposed between the anode and the cathode, wherein the layer including an organic compound contains at least one kind of the benzo[a]fluoranthene compound according to claim 1.

4. The organic light emitting device according to claim 3, wherein the benzo[a]fluoranthene compound is contained in a light emitting layer.

5. The organic light emitting device according to claim 3, further comprising a TFT device.

6. The organic light emitting device according to claim 3, further comprising a color filter.

7. The organic light emitting device according to claim 3, further comprising a TFT device and a color filter.

* * * * *